United States Patent [19]

Narayanan et al.

[11] Patent Number: 4,803,984
[45] Date of Patent: Feb. 14, 1989

[54] METHOD FOR PERFORMING SMALL VESSEL ANASTOMOSIS

[75] Inventors: Krishna Narayanan; Marc D. Liang, both of Pittsburgh, Pa.

[73] Assignee: Montefiore Hospital Association of Western Pennsylvania, Pittsburg, Pa.

[21] Appl. No.: 70,076

[22] Filed: Jul. 6, 1987

[51] Int. Cl.$^4$ .............................................. A61B 17/04
[52] U.S. Cl. .................................................. 128/334 R
[58] Field of Search ............... 128/334 R, 340, 334 C, 128/335, 335.5

[56] References Cited

U.S. PATENT DOCUMENTS

| | | | |
|---|---|---|---|
| 1,470,707 | 10/1923 | Bates | 128/334 R |
| 2,897,820 | 8/1959 | Tauber | 128/340 |
| 4,006,747 | 2/1977 | Knonenthal | 128/335 |
| 4,352,358 | 10/1982 | Angelchik | 128/334 R |
| 4,392,495 | 7/1983 | Bayers | 128/334 R |
| 4,474,181 | 10/1984 | Schenck | 128/334 R |
| 4,553,543 | 11/1985 | Amarasinghe | 128/334 R |

Primary Examiner—Richard C. Pinkham
Assistant Examiner—Gary Jackson
Attorney, Agent, or Firm—Harry B. Keck

[57] ABSTRACT

A microsurgery tool for use in anastomosis of small vessels has a thin arcuate shaft or tube with a tubular distal end having its tubing cut away to define a trough for receiving the pointed end of a suture needle. The microsurgery tool is inserted between confronting ends of vessels into a first vessel for receiving a suture needle point passing through the outer wall of the first vessel. Thereafter the tool is withdrawn from the space between the vessels and the convex outer surface of the trough engages the outer surface of the second vessel where it supports the wall of the second vessel while the point of the same suture needle is passed through the inner wall of the second vessel.

6 Claims, 3 Drawing Sheets

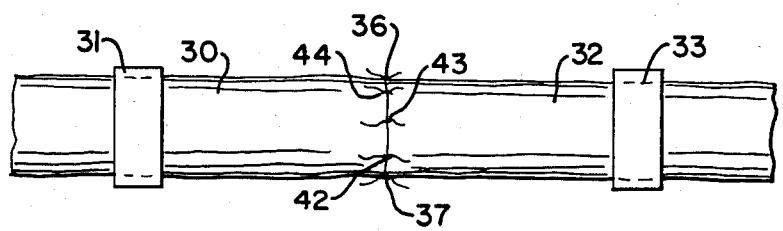
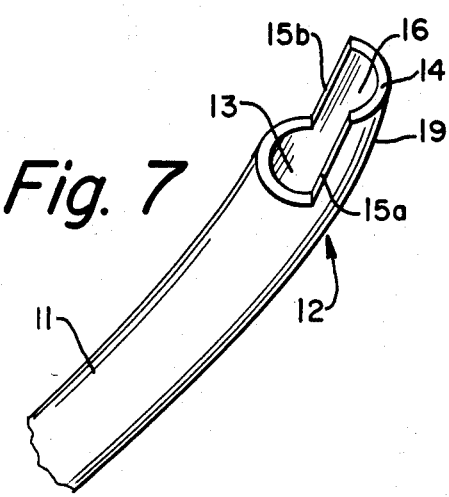
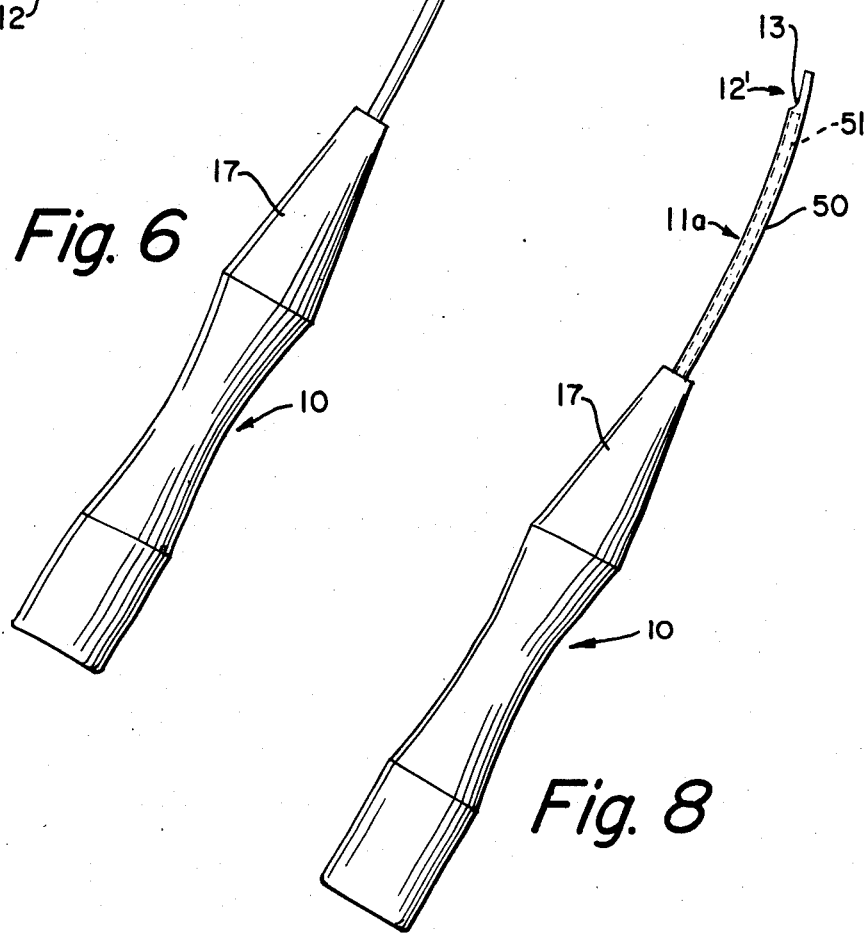

METHOD FOR PERFORMING SMALL VESSEL ANASTOMOSIS

BACKGROUND OF THE INVENTION

1. Field of the Invention

This invention relates to a method for anastomosizing small vessels.

2. Description of the Prior Art

Microsurgery procedures require anastomosis of small vessels, e.g., veins and arteries, which may have a diameter of 0.4-1.5 millimeters. When open ends of such small vessels are to be joined (anastomosis) the recommended procedure is to provide 6-to-8 sutures for a vein-to-vein connection and 7-to-9 sutures for an artery-to-artery connection. Typical sutures are 0.3 to 0.4 millimeters wide. Because of the size of the vessels and sutures, these procedures are carried out with use of a microscope and are referred to as microsurgery techniques.

Overwhelmingly, such anastomosis procedures employ a clamping device which secures the cut ends of the vessel in alignment. See U.S. Pat. No. 4,553,542. A normal procedure employs microsurgery forceps which are inserted through the open end into one of the vessels and allowed to spring open whereby the vessel end region is dilated to facilitate puncturing that vessel with a suture needle. The forceps are withdrawn and inserted through the open end of the other vessel for dilation and the suture needle point punctures the dilated vessel surface. The suture needle is extracted from both vessels and the trailing suture is tied. This sequence is repeated numerous times for each vessel. The initial sutures are usually spaced diametrically apart on the vessels and can be applied without significant difficulty. Subsequent sutures however are quite difficult with the microsurgery forceps technique because of the small size of the vessels. Typically, anastomosis of a single vessel using the microsurgery forceps techniques may require about one hour of surgical time. The success of overall surgical procedures frequently depends upon the success of blood vessel anastomosis procedures. An alternative existing procedure employs a ring device which is mounted annularly from the anastomosis site as described in U.S. Pat. No. 4,474,181. This procedure dilates the ends of the vessels and maintains the anastomosis suture connection in a dilated condition by connecting each suture to the annular ring. Each suture is normally applied with the microsurgery forceps technique when a ring device is used.

In co-pending patent application Ser. No. 914,164, which is assigned to the Assignee of this patent application, an anastomosis tool is described which resembles a tack-lifter having a thin shaft and a pair of projecting tines which receive the point of a suture needle penetrating an open end of a first small vessel and divert the suture needle point toward the open end of a second vessel; the tool then is positioned on the outer surface of the second vessel end to support the second vessel wall while the suture needle point is forced outwardly through the second vessel wall.

STATEMENT OF THE PRESENT INVENTION

A microsurgery tool is provided which functions in cooperation with a suture needle in a small vessel anastomosis. The microsurgery tool has a thin shaft or tube with a tubular distal end portion. The distal end portion is inserted into an open first end of two aligned vessel ends. A surgical needle point is inserted through the outer wall of the first vessel into the tubular distal end of the microsurgery tool and is directed by the tool through the first vessel open end. Thereupon the microsurgery tool is withdrawn and placed on the second vessel outer wall; the suture needle point punctures the inner wall of the second vessel and appears near the distal end of the microsurgery tool. Thereafter the microsurgery tool is withdrawn, the suture needle is advanced through both vessels and the trailing suture is tied. The procedure is repeated as many times as required to provide a satisfactory anastomosis.

DESCRIPTION OF THE DRAWINGS

FIGS. 1, 2, 3, 4, 5 illustrate two vessel ends secured by clamping devices in abutment, and show the use of the tool of this invention in practicing the method of this invention.

FIG. 6 is an enlarged perspective view of one embodiment of the microsurgery tool.

FIG. 7 is an enlarged perspective view of the distal end of the microsurgery tool.

FIG. 8 is an enlarged perspective illustration of a preferred embodiment of the present microsurgery tool.

DESCRIPTION OF THE PREFERRED EMBODIMENTS

Figure 1:
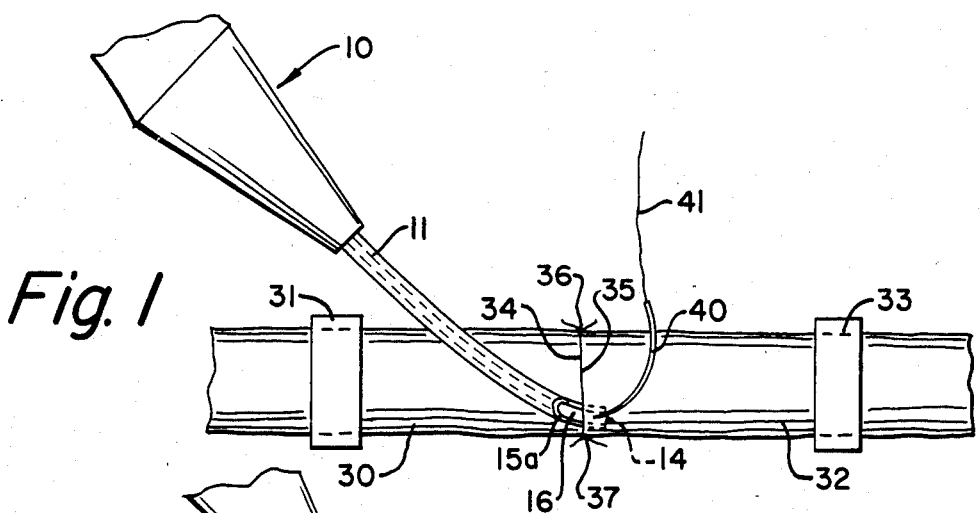

The microsurgery tool 10 of this invention is partially illustrated in one embodiment in FIG. 6 which shows an arcuate, thin shaft or tube 11 and a tubular distal end portion 12. The distal end portion 12 (FIG. 7), has a bore 13, an arcuate forward edge 14 and side surfaces 15a, 15b which define the edges of a trough 16 for receiving the pointed end of a suture needle. The shaft or tube 11 is secured to holding means, e.g., a handle 17. The shaft or tube 11 of the microsurgery tool as shown in FIG. 8 is preferably a plastic tube 50 having in its bore 13 an arcuate plastic or metal wire 51 which extends from the handle 17 through the length of the tube 50, terminating at the distal end portion 12' to define the open bore 13. The shaft or tube 11 preferably is from 1 to 4 millimeters outer diameter and about 10 to 30 millimeters long. The shaft or tube 11 is preferably arcuate to facilitate entry into the vessels. The side walls 15a, 15b extend from the arcuate forward edge 14 for about 1 to 3 millimeters, providing a trough opening about 0.5 to 2 millimeters deep. The distal end portion 12 has a convex outer surface 19 which is also the outer wall of the trough 16.

The handle 17 resembles a pencil and is of such size and shape to permit handling by an operating surgeon. The side walls of the handle 17 may be circular in cross-section, or preferably, may define an equilateral figure such as a hexagon, octagon.

The operation of the present microsurgery tool will be described in relation to FIGS. 1 through 5 inclusive.

In those drawings, a left vessel 30 is secured by a clamping member 31 in abutment with a right vessel 32 which is secured by a clamping member 33. The open ends 34, 35 of the vessels 30, 32 respectively are confined in abutment by means of the clamping members 31, 33. Typical clamping members are shown in U.S. Pat. No. 4,553,542.

To initiate the anastomosis method, two sutures 36, 37 are provided in the vessels 30, 31 in accordance with normal prior art procedures, preferably by employing microsurgery forceps to dilate end vessel openings 34, 35 respectively. The two sutures 36, 37 are spaced apart on the periphery of the open ends 34, 35 and retain the vessels 30, 32 to permit completion of the anastomosis. The distal end portion 12 of the microsurgery tool 10 is introduced between the open ends 34, 35 of the vessels 30, 32 and the trough 16 is positioned within the right-hand vessel 32 beneath its open end 35. The edges 15a, 15b of the trough 16 engage the inner wall of the right-hand vessel 32. Penetration of the distal end portion 12 into the right-hand vessel is about 1.0 millimeter. A portion of the trough 16, approximately 0.5 to 1.5 millimeter, is maintained outside the right-hand vessel and is visible to the operator. An arcuate suture needle 40 with a trailing suture 41 is introduced to the site with its point penetrating the outer wall of the right-hand vessel 32 in the region of the trough 16. The open trough 16 receives the point of the arcuate suture needle 40 and directs the point out from the open end 35 of the right-hand vessel 32.

Figure 2:
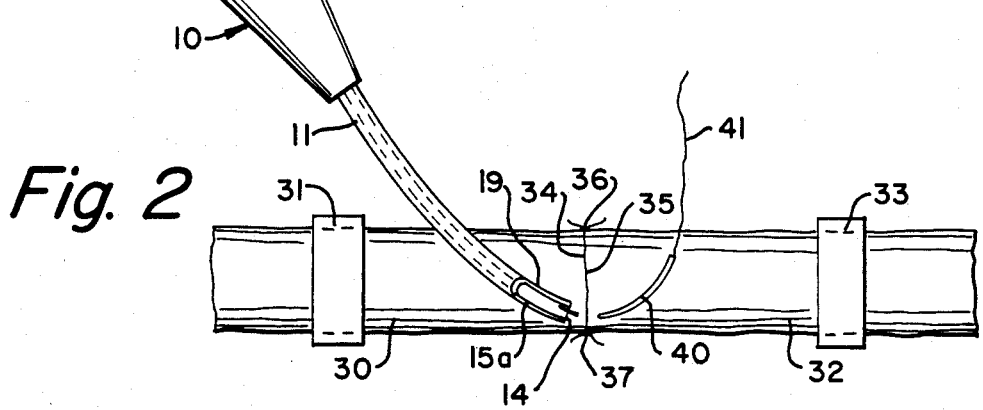
Figure 3:
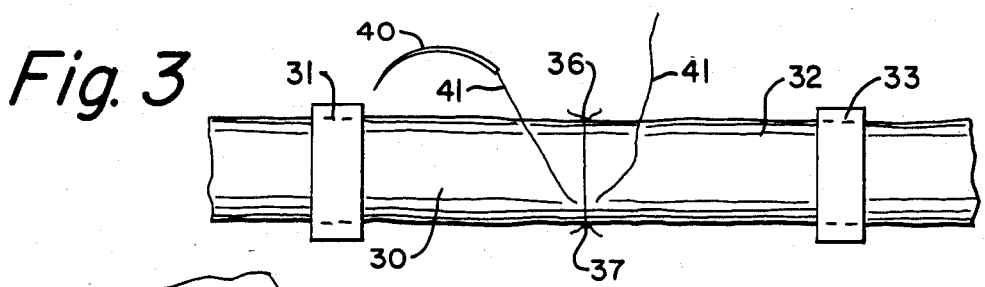
Figure 4:
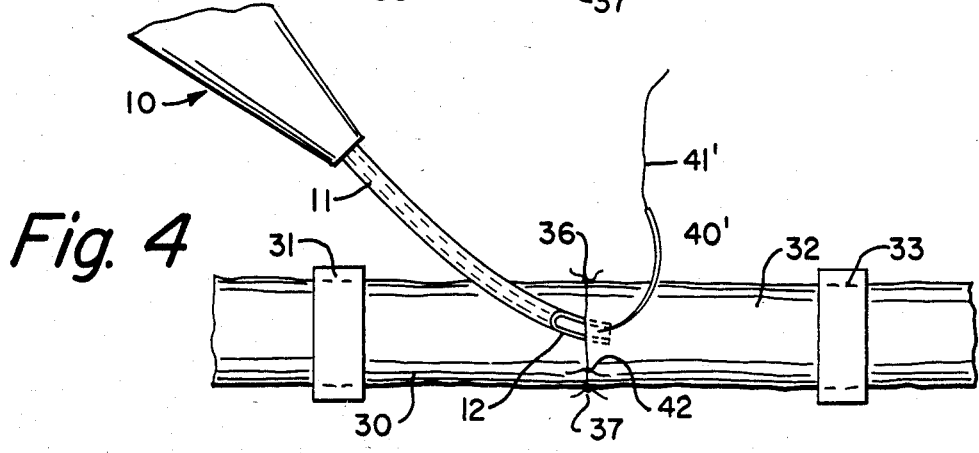

The microsurgery tool 10 is then withdrawn from the opening between the open ends 34, 35 and is positioned as shown in FIG. 2 with its convex surface 19 engaged with the outer wall of the left-hand vessel 30. The arcuate suture needle 40 punctures the inner wall of the left-hand vessel 30 forwardly of the arcuate edge 14 and penetrates the vessel wall upwardly, guided by the tool 10. Thereafter the microsurgery tool 10 is withdrawn from the site and the arcuate suture needle 40 is extracted through the suture openings in the vessels 30, 32 with the trailing suture 41 being drawn into a position where the suture ends 41 (FIG. 3) can be tied to form a suture 42 as shown in FIG. 4. Thereafter the microsurgery tool 10 is introduced into the opening between the open ends 34, 35 and contacts the inner wall of the right-hand vessel 32. The microsurgery tool 10 is used in combination with an arcuate suture needle 40' which is secured to a trailing suture 41' and the process described in FIGS. 1, 2, 3 is repeated to produce an additional suture 43 as shown in FIG. 5.

When the anastomosis is complete, uniform sutures (36, 37, 42, 43, 44, as shown in FIG. 5) along with other sutures (not seen in FIG. 5) will present the required number of sutures.

The shaft or tube 11 preferably is formed from transparent plastic tubing having an outer diameter of 0.5 to 1.5 mm. It may be preferred to provide a set of several microsurgery tools of differing dimensions (lengths, arcuate shape and tubing diameter) as might be required to complete related anastomosis procedures. Typical suture needles in blood vessel anastomosis procedures are No. 10 (100 microns thickness) and No. 11 (75 microns thickness). The trough 16 of the microsurgery tool 10 should be large enough to receive the cooperating suture needles. Preferably the tools 10 are discarded after use with one patient. The shafts or tubes 11 are permanently secured in holding elements 17.

Figure 9:
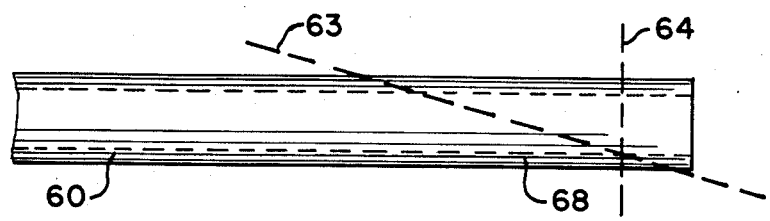
FIGS. 9, 10, 11 are enlarged perspective illustrations of a plastic tube showing different cutting patterns to produce a distal end of the microsurgery tool.
Figure 12:
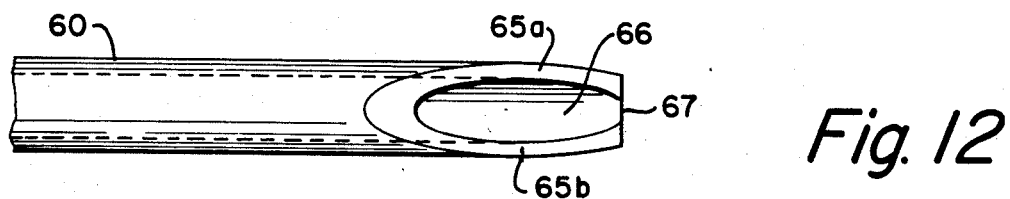
FIGS. 12, 13, 14 are perspective illustrations of the distal end of a microsurgery tool resulting from the procedures of FIGS. 9, 10, 11 respectively.

As shown in FIG. 9, a plastic tube 60 may be cut along the planes indicating at 63 and 64. The sequence of cuts is not significant. The resulting plastic tube end, shown in FIG. 12 includes side walls 65a, 65b, a trough 66 and a forward arcuate end surface 67. A convex surface 68 (FIG. 9) is retained beneath the trough 66.

Figure 10:
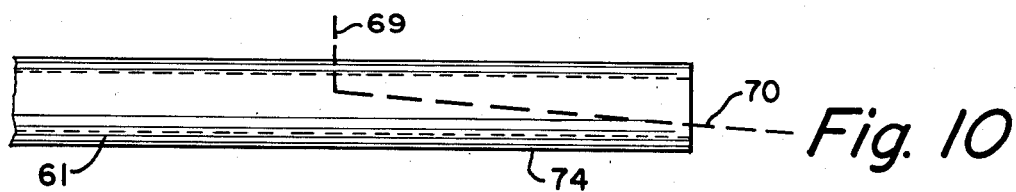
Figure 13:
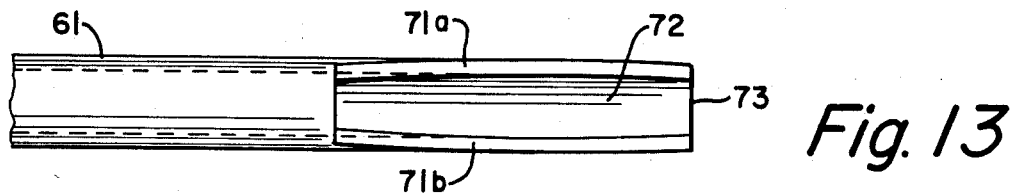

Alternatively a plastic tube 61 as shown in FIG. 10 may be cut along the planes 69, 70. The sequence of cutting is not significant. The resulting plastic tube end, as shown in FIG. 13, will have side walls 71a, 71b, defining a trough 72 and a forward arcuate surface end 73. A convex surface 74 (FIG. 10) is retained beneath the trough 72.

Figure 11:
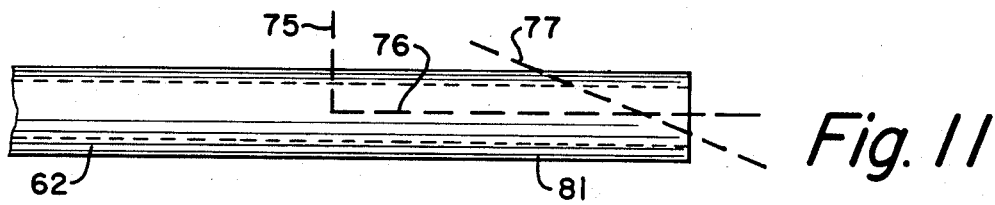
Figure 14:
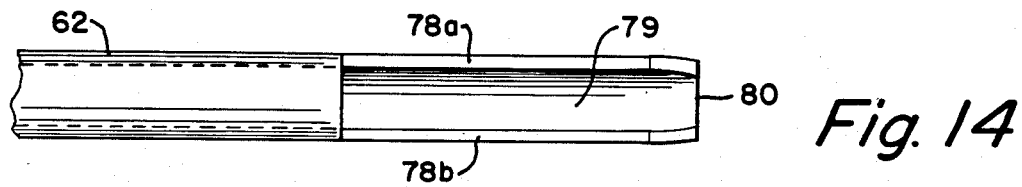

A further alternative shown in FIG. 11 provides three cuts in a plastic tube 62 along the planes 75, 76, 77. The sequence of cuts is not significant. The resulting end is shown in FIG. 14 wherein side walls 78a, 78b define a trough 79 and an arcuate forward end surface 80. A convex surface 81 (FIG. 11) is retained beneath the trough 79.

In all of the embodiments illustrated in FIGS. 9 through 14, it may be desirable to abrade any sharp edges resulting from the cuts. As a further alternative to tube cuts, a section of tubing may be abraded to define the desired trough and forward end.

In the improved method of this invention, anastomosis procedures are accelerated and are completed without excessive deformation of the vessels. Because of the close tolerances in the anastomosis procedure for small vessels, the microsurgery tool achieves a positive penetration of a suture needle in both vessels which are being connected. The preferred transparent tubing facilitates the procedure by permitting the operator to view the suture needle point as it emerges within the first vessel. The tool limits damage to the interior of the vessel which might result from errant movement of the suture needle.

The procedure is illustrated in FIGS. 1-5 inclusive for a butt-to-butt connection of two vessels. It should be understood that essentially the same procedure can be carried out with an end-to-side anastomosis of the type which is well known in the art and which is illustrated, for example, in the aforementioned U.S. Pat. No. 4,474,181. In said end-to-side anastomosis, one vessel has a transverse cut end and the other vessel is continuous with an opening in its side wall.

The present microsurgery tool as well as the anastomosis procedure can employ the anastomosis ring described in U.S. Pat. Nos. 4,474,181 and 4,553,542.

We claim:

1. A method for anastomosizing two small vessels comprising:

securing an open end of a first vessel in confronting relation with an opening in a second vessel at the anastomosis site;

introducing the tubular distal end portion of a microsurgery tool having an open trough between the two vessels and into said first vessel;

extending the point of a suture needle through the wall of said first vessel into the open trough of said distal end portion and advancing the said point toward the shaft of said microsurgery tool;

withdrawing the said distal end portion of said microsurgery tool from said first vessel, engaging the convex surface of said distal end portion on the outer surface of the second vessel;

introducing the point of said suture needle into the said second vessel and penetrating the inner wall of said second vessel with the needle point passing through the wall of said second vessel adjacent to the said convex surface;

withdrawing the said microsurgery tool from said anastomosis site, advancing the said needle with its trailing suture through the wall of said second vessel;

tying the ends of said trailing suture across the confronting openings of said vessels with the confronting vessel ends engaged.

2. The method of claim 1 wherein the two vessels are veins.

3. The method of claim 1 wherein the two vessels are arteries.

4. The method of claim 1 wherein one vessel is a vein and the other vessel is an artery.

5. The method of claim 1 wherein one vessel has a transverse cut end and the other vessel is continuous with an opening in its side wall.

6. The method of claim 1 wherein only a portion of the said trough of the said distal end portion of the said microsurgery tool is introduced into the said first vessel and a portion of the said trough is positioned outside the end of said first vessel and the pointed end of said suture needle is directed by the trough of said distal end portion out from the said first vessel without contacting the inner wall of said first vessel.

* * * * *